(12) United States Patent
Ma et al.

(10) Patent No.: US 12,196,722 B2
(45) Date of Patent: Jan. 14, 2025

(54) DYNAMIC CRACK LEAKING STOPPAGE EVALUATION EXPERIMENT DEVICE AND EXPERIMENT METHOD

(71) Applicant: China University of Petroleum-Beijing, Beijing (CN)

(72) Inventors: Chengyun Ma, Beijing (CN); Yongcun Feng, Beijing (CN); Jingen Deng, Beijing (CN)

(73) Assignee: CHINA UNIVERSITY OF PETROLEUM-BEIJING, Beijing (CN)

( * ) Notice: Subject to any disclaimer, the term of this patent is extended or adjusted under 35 U.S.C. 154(b) by 333 days.

(21) Appl. No.: 17/777,594

(22) PCT Filed: Nov. 25, 2020

(86) PCT No.: PCT/CN2020/131270
§ 371 (c)(1),
(2) Date: May 17, 2022

(87) PCT Pub. No.: WO2022/099785
PCT Pub. Date: May 19, 2022

(65) Prior Publication Data
US 2023/0141812 A1 May 11, 2023

(30) Foreign Application Priority Data
Nov. 11, 2020 (CN) .......................... 202011250799.1

(51) Int. Cl.
*G01N 3/12* (2006.01)
*E21B 21/00* (2006.01)
(Continued)

(52) U.S. Cl.
CPC ............. *G01N 3/12* (2013.01); *E21B 21/003* (2013.01); *E21B 49/00* (2013.01); *G01N 15/02* (2013.01); *G01N 33/24* (2013.01)

(58) Field of Classification Search
CPC ....... G01N 3/12; G01N 15/082; E21B 21/003
See application file for complete search history.

(56) References Cited

FOREIGN PATENT DOCUMENTS

| CN | 201654010 U | * | 11/2010 |
| CN | 201902206 U | * | 7/2011 |

(Continued)

OTHER PUBLICATIONS

First Office Action issued in corresponding Chinese Application No. 202011250799.1; mailed Jun. 2, 2021; 12 pgs.
(Continued)

*Primary Examiner* — Herbert K Roberts
(74) *Attorney, Agent, or Firm* — HAUPTMAN HAM, LLP

(57) ABSTRACT

A dynamic crack leaking stoppage evaluation experiment device includes a crack simulation experiment instrument having a dynamic crack simulation mechanism. The dynamic crack leaking stoppage evaluation experiment device can simulate a dynamic change process of a crack from a closed state to an open state. An experiment method can be applied to study a variation range of the width of the crack that have been subjected to self-adaptive leaking stoppage with various combinations of leaking stoppage materials and under different increments, and the method can also be applied to quantitatively study on effecting patterns of rheological parameters and hydraulic parameters of well drilling fluid on stability of a leaking stoppage layer in the dynamic crack, so that enabled is not only simulation of leaking stoppage process of a dynamic crack, but also real-time monitoring and evaluation on leaking stoppage (Continued)

effect and leaking stoppage location inside the dynamic crack.

10 Claims, 10 Drawing Sheets

(51) Int. Cl.
*E21B 49/00* (2006.01)
*G01N 15/02* (2006.01)
*G01N 15/08* (2006.01)
*G01N 33/24* (2006.01)

(56) References Cited

FOREIGN PATENT DOCUMENTS

| CN | 202975005 U | * | 6/2013 | |
| CN | 103411750 A | | 11/2013 | |
| CN | 103510944 A | | 1/2014 | |
| CN | 104122147 A | * | 10/2014 | |
| CN | 103411750 B | * | 9/2015 | |
| CN | 204877451 U | * | 12/2015 | |
| CN | 205139114 U | * | 4/2016 | |
| CN | 105545249 A | * | 5/2016 | |
| CN | 103510944 B | | 3/2017 | |
| CN | 107102099 A | * | 8/2017 | ......... G01M 99/008 |
| CN | 207974810 U | * | 10/2018 | |
| CN | 208073462 U | * | 11/2018 | |
| CN | 109001438 A | * | 12/2018 | |
| CN | 109269901 A | * | 1/2019 | ......... G01N 15/0826 |
| CN | 208502713 U | * | 2/2019 | ............ E21B 33/03 |
| CN | 109653729 A | * | 4/2019 | ........... E21B 47/005 |
| CN | 209086218 U | * | 7/2019 | |
| CN | 209212232 U | * | 8/2019 | |
| CN | 111122413 A | * | 5/2020 | |
| CN | 210829240 U | * | 6/2020 | |
| CN | 111734407 A | * | 10/2020 | ............ E21B 49/00 |

OTHER PUBLICATIONS

International Search Report issued in corresponding International Application No. PCT/CN2020/131270; mailed Aug. 4, 2021; 4 pgs.

* cited by examiner

DYNAMIC CRACK LEAKING STOPPAGE EVALUATION EXPERIMENT DEVICE AND EXPERIMENT METHOD

RELATED APPLICATIONS

The present application is a U.S. National Phase of International Application Number PCT/CN2020/131270 filed Nov. 25, 2020, and claims priority to Chinese Application Number 202011250799.1, filed Nov. 11, 2020.

FIELD OF THE INVENTION

The present disclosure relates to the technical field of petroleum engineering, in particular to a dynamic crack leaking stoppage evaluation experiment device and an experiment method thereof.

BACKGROUND OF THE INVENTION

In the field of petroleum engineering, well leakage has always been a world-class problem that has plagued domestic and international petroleum exploration and development and has not been completely resolved so far. Most of well drilling processes have different extents of leakage. Severe well leakage would cause drop of borehole pressure, affect normal well drilling, cause instability of well walls, and induce formation fluids to flow into the wellbore and result in well blowout. It has been indicated according to field experience that a success rate of leaking stoppage is less than 30%.

At present, a large number of researchers have studied on different types of leakage problems, and have proposed various materials of leaking stoppage agents and have evaluated leaking stoppage effects of these leaking stoppage agents. However, existing devices and methods for evaluating leaking stoppage agent materials can only perform qualitative evaluation and analysis on cracks with fixed fracture sizes, but in actual well drilling processes where most of cracks are initially in a closed state, only upon the action of pressure difference of well drilling fluid, can the cracks expand gradually, and then can the leaking stoppage materials in the well drilling fluid enter the cracks and apply bridging-plugging on the cracks. In addition, existing crack leaking stoppage evaluation devices are incapable of monitoring leaking stoppage speed and determining leaking stoppage location in real time, so that they can neither evaluate performance of leaking stoppage materials, leaking stoppage effect, proportioning relationship among leaking stoppage agent materials, and lamination ability of a leaking stoppage layer, nor monitor and evaluate the leaking stoppage speed, the leaking stoppage effect and the leaking stoppage location in real time.

SUMMARY OF THE INVENTION

In view of the above problems, an objective of the present disclosure is to provide a dynamic crack leaking stoppage evaluation experiment device and an experiment method thereof, so as to solve the problem that the existing crack leaking stoppage evaluation device fails to conduct experiments due to incapable of simulating dynamic changes of morphology of a mud shale crack.

The present disclosure provides a dynamic crack leaking stoppage evaluation experiment device, which includes a crack simulation experiment instrument, a fluid reservoir tank, a recycle pool, a hydraulic pump, a hand pump, a fluid weighting electronic balance, an inlet pressure gauge, an outlet pressure gauge, a first back pressure back valve, and a second back pressure valve; an upper part of the crack simulation instrument is provided with a fluid inlet and a fluid outlet, and a bottom of the crack simulation instrument is provided with a fluid seepage port; a fluid outlet of the fluid reservoir tank is communicated with a fluid inlet of the hydraulic pump through a pipeline, and a fluid outlet of the hydraulic pump is communicated with a fluid inlet of the crack simulation instrument through an input pipeline; the inlet pressure gauge is provided on the input pipeline; a fluid outlet of the crack simulation experiment instrument is connected to upright an upper part of the recycle pool through an output pipeline, and a fluid outlet end of the output pipeline is provided with the first back pressure valve; the outlet pressure gauge is provided on the output pipeline; the fluid seepage port is provided with a drain pipe, and the second back pressure valve is provided on the drain pipe; the fluid weighing electronic balance is provided with a fluid weighing container which is arranged upright below an outlet of the drain pipe; the hand pump is communicated with an air inlet provided on a side wall of a cylinder body; when the hand pump supplies a pressure to a annular space formed between a rubber sleeve and the cylinder body, due to deformability of the rubber sleeve, the pressure input by the hand pump can smoothly transfer to a rock-mass sample to enable a radial pressure to be applied on the rock-mass sample.

Preferably, the crack simulation experiment instrument includes the cylinder body, an upper cover, a lower cover, an upper plug, a lower plug, an indenter, and the rubber sleeve; the upper cover and the lower cover are arranged at top and bottom ends of the cylinder body, respectively, the upper plug and the lower plug are arranged inside the cylinder body and closely attached to the upper cover and the lower cover, respectively; the upper plug, the lower plug and the cylinder body jointly enclose an accommodating cavity, a geometric size of which can properly accommodate the rock-mass sample; a fluid inlet and a fluid outlet are provided on both sides of the upper cover, respectively, a fluid inlet channel slot is provided between the fluid inlet and the accommodating cavity, and the fluid inlet channel slot sequentially passes through, from outside to inside, the upper cover and the upper plug that are on the side close to the fluid inlet; a fluid outlet channel slot is provided between the fluid outlet and the accommodating cavity, and the fluid outlet channel slot sequentially passes through, from inside to outside, the upper plug and the upper cover that are on the side close to the fluid outlet; a junction slot is provided between the fluid inlet channel slot and the fluid outlet channel slot of the upper plug, and the junction slot is communicated with the accommodating cavity.

Preferably, the crack simulation experiment instrument is equipped with a dynamic crack simulation mechanism which includes a rock-mass sample, a fixed plate, two seam plates, multiple sets of springs, and a sealing rubber sleeve; the rock-mass sample is provided with a hollow groove inside, and an upper part of the hollow groove is communicated with a fluid inlet channel of the dynamic crack simulation mechanism; the fixing plate is fixed on a side wall and a bottom of the hollow groove; the two seam plates are arranged symmetrically with respect to a center line of the hollow groove, bottom ends of the two seam plates are both pivotally connected to the fixing plate arranged at the bottom of the hollow groove, and top ends of the two seam plates both touch a top surface of the hollow groove; when the two seam plates are in a closed state, the top ends of the two seam plates splice with each other to form an inverted corner; the sealing rubber sleeve is laid on outer surfaces of the seam plates; the sealing rubber sleeve extends, from bottom to top, from the bottom ends of the seam plates to contact points between the top ends of the seam plates and the top surface of the hollow groove, so as to enable complete sealing of the seam plates from the rock-mass sample; center lines of the fluid inlet channel slot and the fluid outlet channel slot are located on one same line, and a line connecting the fluid inlet channel slot and the fluid outlet channel slot is communicated with the junction slot in a cross-shape pattern; the fluid seepage port is provided at the bottom of the lower cover, a fluid seepage channel is provided between the fluid seepage port and the accommodating cavity, and the fluid seepage channel sequentially penetrates middle parts of the lower plug and the lower cover; several sets of springs are arranged between the seam plates and the fixing plate arranged at the side wall of the hollow groove, each set of springs includes two springs located at an identical height, and ends of each spring are respectively fixed on the sealing rubber sleeve and the fixed plate; one of the seam plates is provided with a plurality of pressure measuring points at intervals, and each pressure measuring point is provided with a pressure sensor which extends to outside through a wire and is provided with a pressure sensor connector; after leaking stoppage slurry enters the hollow groove of the rock-mass sample from the fluid inlet channel of the dynamic crack simulation mechanism, the leaking stoppage slurry enters the inverted corner at the top ends of the two seam plates and expands the two seam plates apart from each other to rotate to both sides around the fixed plate, so as to dynamically simulate an aperture-gap cracking process.

Preferably, the rubber sleeve is provided at an inner wall of the cylinder body and at connections between the cylinder body and the upper plug, the lower plug, the rubber sleeve divides the cylinder body into two closed spaces, that are, respectively, an annular space formed between the rubber sleeve and the cylinder body and a space enclosed by the rubber sleeve, the upper plug and the lower plug; the side wall of the cylinder body is provided with an air inlet which is communicated with the annular space formed between the rubber sleeve and the cylinder body.

The present disclosure further discloses an experiment method for obtaining crack dynamic changes of a crack plugged with fluid medium, which adopts the above-mentioned dynamic crack leaking stoppage evaluation experiment device and includes steps of:

Step A, assembling a crack simulation instrument;
Step A1, assembling the rock-mass sample, the fixed plate, the two seam plates, the multiple sets of springs, and the sealing rubber sleeve into a dynamic crack simulation mechanism;
Step A2, installing the lower plug, the dynamic crack simulation mechanism, and the upper plug within the rubber sleeve in sequence to assemble them into the crack simulation instrument; and
Step A3, turning the upper cover and the lower cover to make the rock-mass sample generate an axial stress;
Step B, sealing the accommodating cavity, and setting valve values of the first back pressure valve and the second back pressure valve and a flow rate of the hydraulic pump;
Step C, plugging a crack with clean water or leaking stoppage slurry to obtain dynamic change process of the crack; and
Step D, evaluating dynamic crack leaking stoppage effect, wherein evaluation on the dynamic crack leaking stoppage effect includes quantitative evaluation on leaking stoppage location and dynamic pressure bearing capacity of the leaking stoppage slurry under scouring action of the leaking stoppage slurry, evaluation on an effect of fluid rheological parameters on stability of the second leaking stoppage layer after circulating fluid is replaced in the subsequent well drilling process, and evaluation an effect of hydraulic parameters of the leaking stoppage slurry on the stability of the second leaking stoppage layer.

Further, plugging a crack with clean water to obtain dynamic change process of the crack specifically includes steps of:

Step C11, activating the hydraulic pump so that clean water enters, via the fluid inlet, the crack simulation experiment instrument successively through the fluid reservoir tank, the hydraulic pump, and the input pipeline in sequence, wherein a portion of the clean water enters the crack by passing through the fluid inlet channel slot, the junction slot, and the fluid inlet channel and the inverted corner of the crack simulation mechanism, and then reaches the second back pressure valve by passing through the fluid seepage channel and the fluid seepage port; and wherein the other portion of the clean water reaches the first back pressure valve by passing through the fluid outlet channel slot, the fluid outlet and the output pipeline;

Step C12, forming, by the injected clean water, a hydraulic pressure gradually at the fluid inlet channel and the inverted corner; and Step C13, expanding, when the hydraulic pressure exceeds an elastic force of the springs, the two seam plates apart from each other gradually, wherein as the hydraulic pressure at the fluid inlet channel and the inverted corner increases, an opening degree of the crack formed by expanding the two seam plates increases gradually until the hydraulic pressure exceeds a pressure value of 1.5 MPa set for the second back pressure valve, then the opening degree of the crack formed by the two seam plates changes no longer.

Further, plugging a crack with leaking stoppage slurry to obtain dynamic change process of the crack specifically includes steps of:

Step C21, filling the reservoir tank with leaking stoppage slurry;

Step C22, activating the hydraulic pump so that the leaking stoppage slurry in the reservoir tank enters, via the fluid inlet, the crack simulation instrument through the hydraulic pump and the input pipeline, wherein a portion of the leaking stoppage slurry enters the crack by passing through the fluid inlet channel slot, the junction slot, and the fluid inlet channel slot and the inverted corner of the crack simulation mechanism, and then reaches the second back pressure valve by passing through the fluid seepage channel and the seepage port; and wherein the other portion of the leaking stoppage slurry reaches the first back pressure valve by passing through the fluid outlet channel slot, the fluid outlet and the output pipeline;

Step C23, accumulating the leaking stoppage slurry gradually within the inverted corner to form a hydraulic pressure;

Step C24, expanding, when the hydraulic pressure at the inverted corner exceeds an elastic force of the springs, the two seam plates apart from each other gradually, wherein as the hydraulic pressure inside the crack simulation mechanism increases, an opening degree of a crack formed by expanding the two seam plates increases gradually until the hydraulic pressure exceeds a pressure value of 1.5 MPa set for the second back pressure valve, then the opening degree of the crack formed by the two seam plates changes no longer; at the same time, particles in the leaking stoppage slurry form a leaking stoppage layer in a channel of the crack;

Step C25, injecting the leaking stoppage slurry continuously into the fluid inlet channel and the inverted corner to form a hydraulic pressure which increases gradually, wherein under the action of the hydraulic pressure, the two seam plates are further expanded apart, so that the leaking stoppage layer is damaged or a location of the leaking stoppage layer is transferred, and a second leaking stoppage layer is newly formed; and Step C26, recording change of a pressure value of the pressure sensor as a function of time, and recording, when it is observed that the pressure value of the pressure sensor changes suddenly, a position of a pressure measurement point on the seam plate that corresponds to the pressure sensor to determine leaking stoppage location of the leaking stoppage slurry in the crack.

Further, the quantitative evaluation on leaking stoppage location and dynamic pressure bearing capacity of the leaking stoppage slurry under scouring action of the leaking stoppage slurry is implemented after plugging the crack with the leaking stoppage slurry to obtain dynamic change process of the crack, and specifically includes steps of:

Step X1, adjusting, after a stable second leaking stoppage layer is formed, a pressure value of the first back pressure valve to be equal to a value of the inlet pressure gauge;

Step X2, leading the excess leaking stoppage slurry into the recycle pool through the first back pressure valve, so that the leaking stoppage slurry inside the fluid inlet channel and the inverted corner of the crack simulation mechanism forms a dynamic flow which causes continuous scour flow onto the leaking stoppage layer until the second leaking stoppage layer is damaged;

Step X3, subjecting the second leaking stoppage layer to damage gradually, so that the value of the inlet pressure gauge is varied and a width of the crack decreases;

Step X4, stopping, once a pressure at the fluid inlet channel and the inverted corner of the crack simulation mechanism is lower than the pressure value of the first back pressure valve, the leaking stoppage slurry dynamic flowing, plugging the crack once again, and then repeating the Steps X2 to X3; and Step X5, recording change of the pressure value of the pressure sensor as a function of time, and recording, when it is observed that the pressure value of the pressure sensor changes suddenly, a position of a pressure measurement point on a seam plate that corresponds to the pressure sensor to determine leaking stoppage location of the leaking stoppage slurry in the crack.

Further, the evaluation on an effect of fluid rheological parameters on stability of the second leaking stoppage layer after circulating fluid is replaced in the subsequent well drilling process is implemented after plugging the crack with the leaking stoppage slurry to obtain dynamic change process of the crack, and specifically includes a step of:

Step Y, stopping, after a stable second leaking stoppage layer is formed, the hydraulic pump, and replacing the leaking stoppage slurry with clean water, water-based well drilling fluid or oil-based well drilling fluid, and adjusting the pressure value of the first back pressure valve to be equal to a value of the inlet pressure gauge that is before stopping the pump.

Further, the evaluation on an effect of hydraulic parameters on stability of the leaking stoppage slurry of the second leaking stoppage layer is implemented after plugging the crack with the leaking stoppage slurry to obtain dynamic change process of the crack, and specifically includes steps of:

Step Z1, adjusting, after a stable second leaking stoppage layer is formed, the pressure value of the first back pressure valve to be equal to a value of the inlet pressure gauge, and leading the excess leaking stoppage slurry into the recycle pool through the first back pressure valve so that the leakage leaking stoppage slurry inside the fluid inlet channel and the inverted corner of the crack simulation mechanism form a dynamic flow;

Step Z2, increasing a flow rate of the hydraulic pump to 3 L/min and keeping for 1 h;

Step Z3, increasing the flow rate of the hydraulic pump to 4 L/min and still keeping for 1 h;

Step Z4, increasing the flow rate of the hydraulic pump with an increment of 1 L/min per hour until the leakage stoppage layer is damaged;

Step Z5, recoding change of the pressure value of the pressure sensor as an function of time, and recording, when it is observed that the pressure value of the pressure sensor changes suddenly, a position of a pressure measurement point on a seam plate that corresponds to the pressure sensor to determine leaking stoppage location of the leaking stoppage slurry in the crack; and Step Z6, plotting a curve regarding a relationship between the pressure value of the pressure measuring point on the seam plate and the flow rate.

DETAILED DESCRIPTION OF THE EMBODIMENTS

The following embodiments are used to illustrate the present disclosure, but are not intent to limit the protection scope of the present disclosure.

Embodiment 1

Provided in Embodiment 1 is a dynamic crack leaking stoppage evaluation experiment device, a structure of which is described in detail below.

Figure 1:
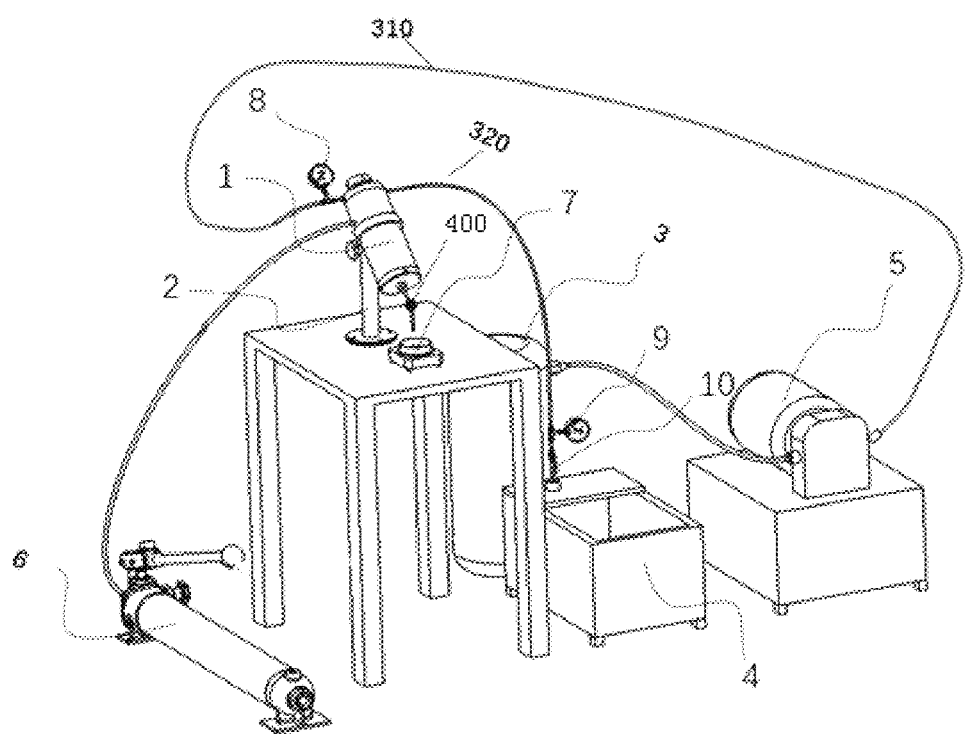
FIG. 1 is a schematic diagram of a structure of a dynamic crack leaking stoppage evaluation experiment device according to Embodiment 1 of the present disclosure.
Figure 2:
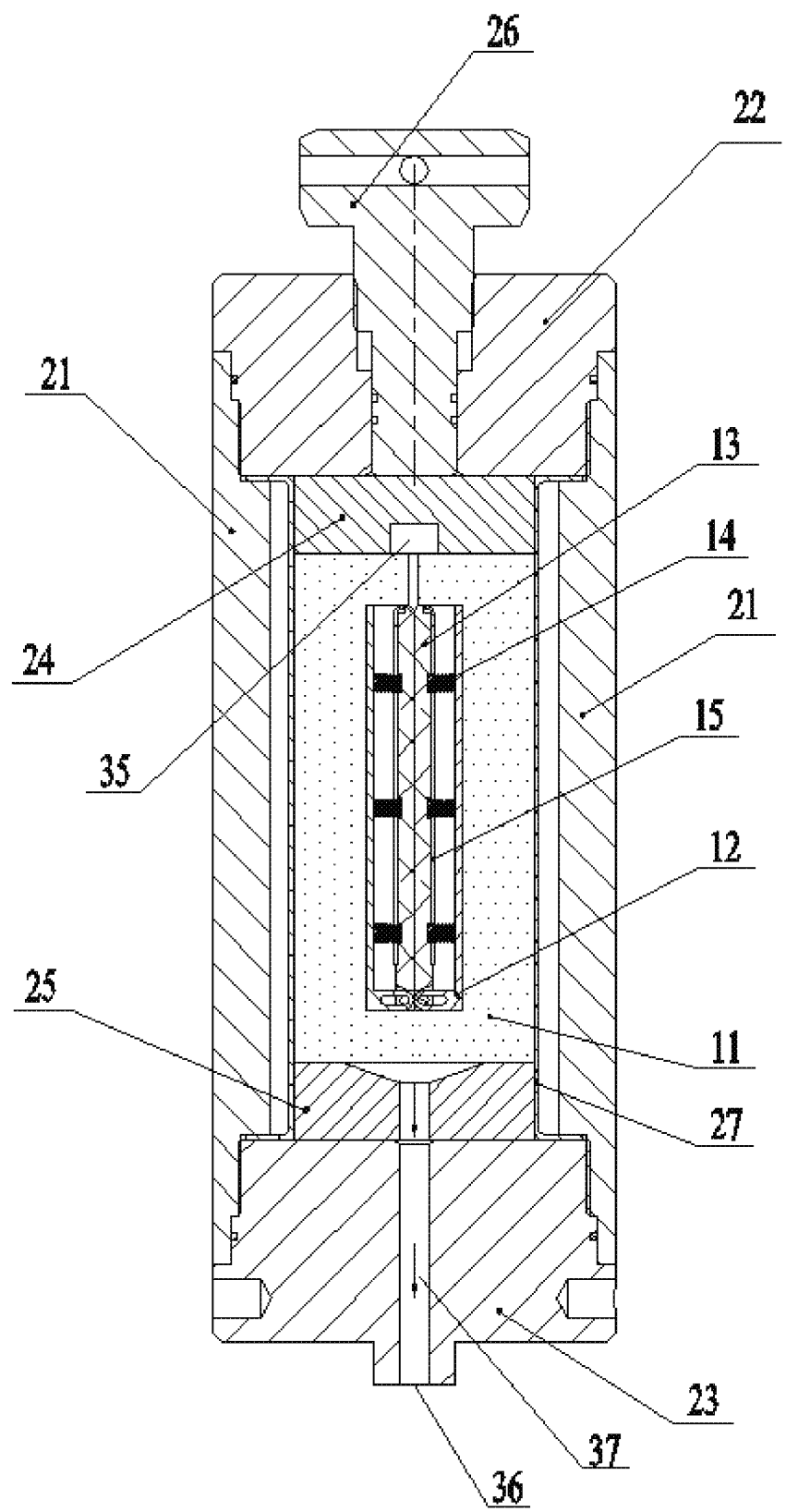
FIG. 2 is a cross-sectional view of a dynamic crack simulation mechanism provided in a crack simulation experiment instrument according to Embodiment 1 of the present disclosure.
Figure 3:
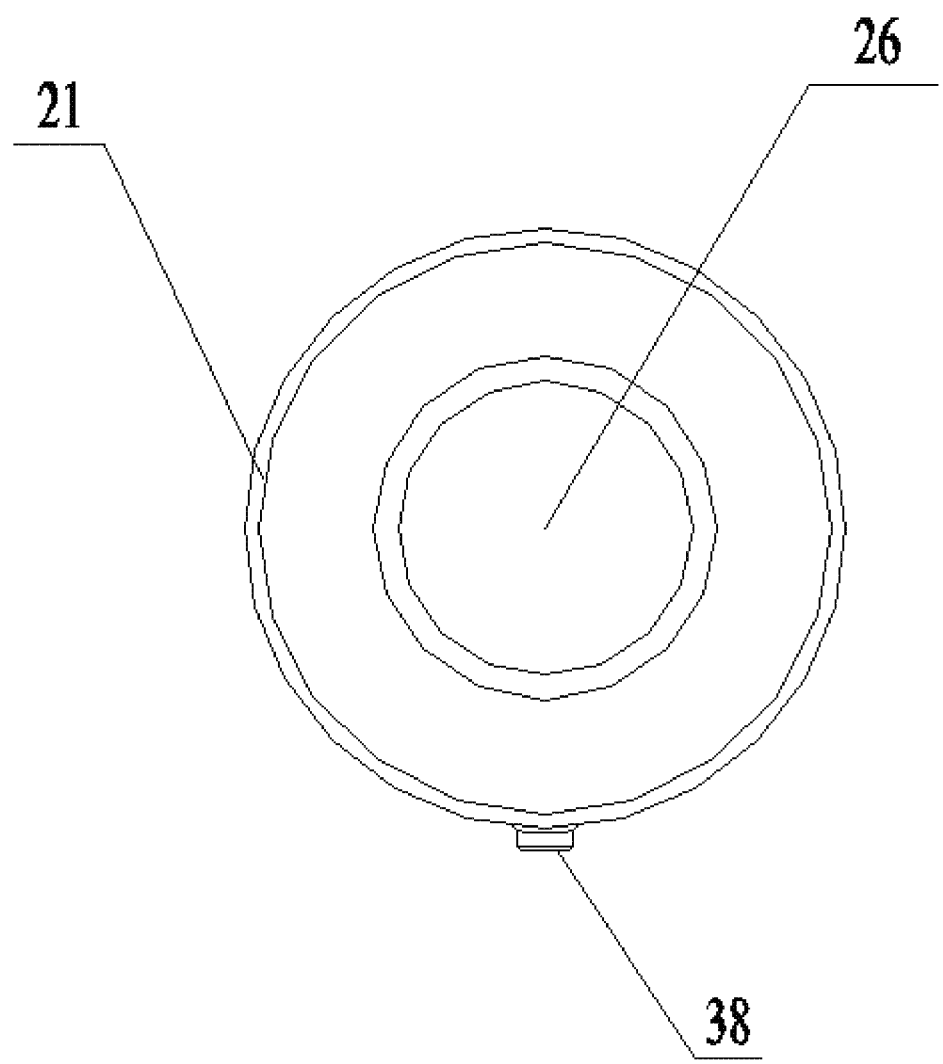
FIG. 3 is a top view of the crack simulation experiment instrument according to Embodiment 1 of the present disclosure.
Figure 4:
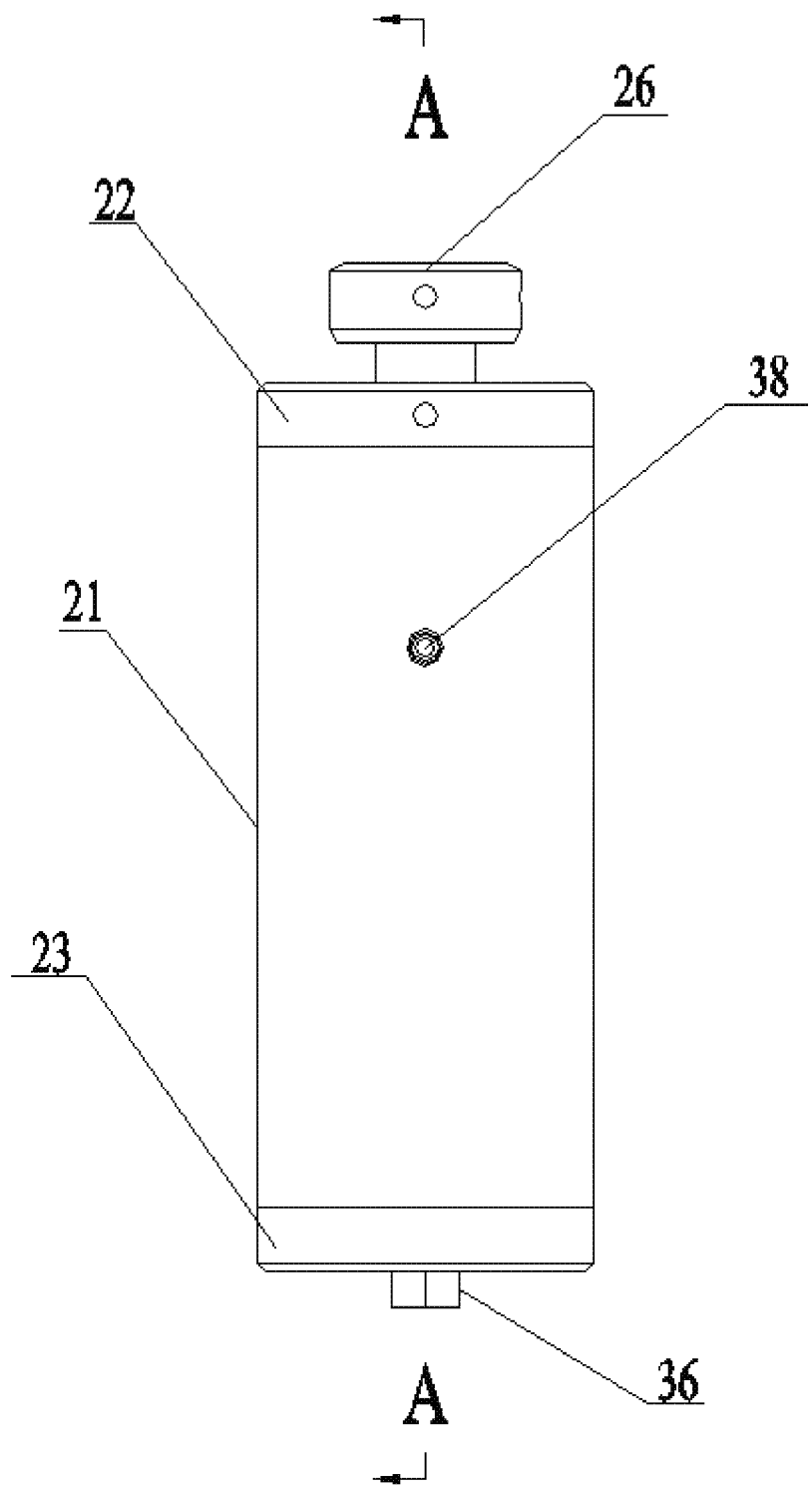
FIG. 4 is a front view of the crack simulation experiment instrument according to Embodiment 1 of the present disclosure.
Figure 5:
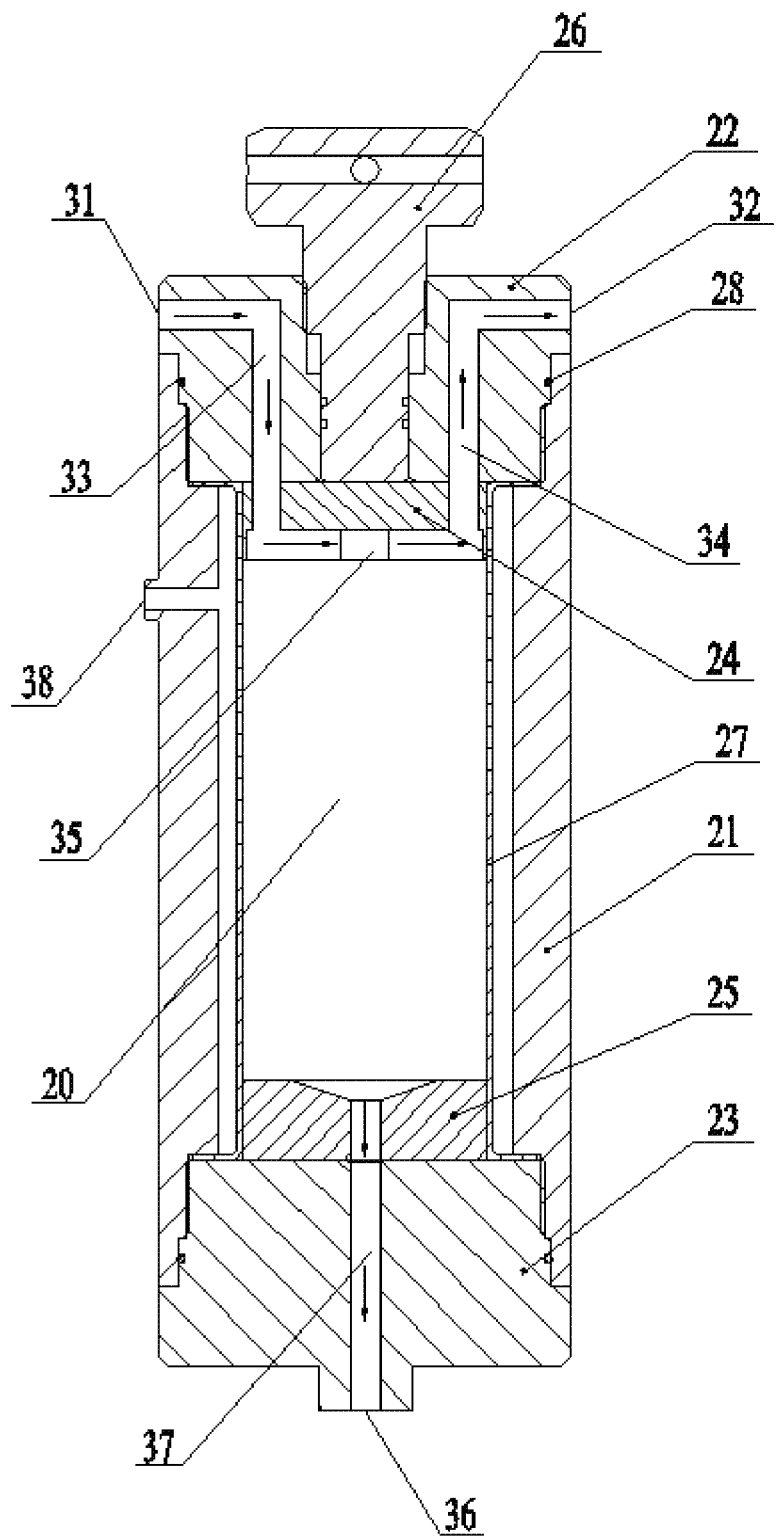
FIG. 5 is a cross-sectional view along A-A in FIG. 4.
Figure 6:
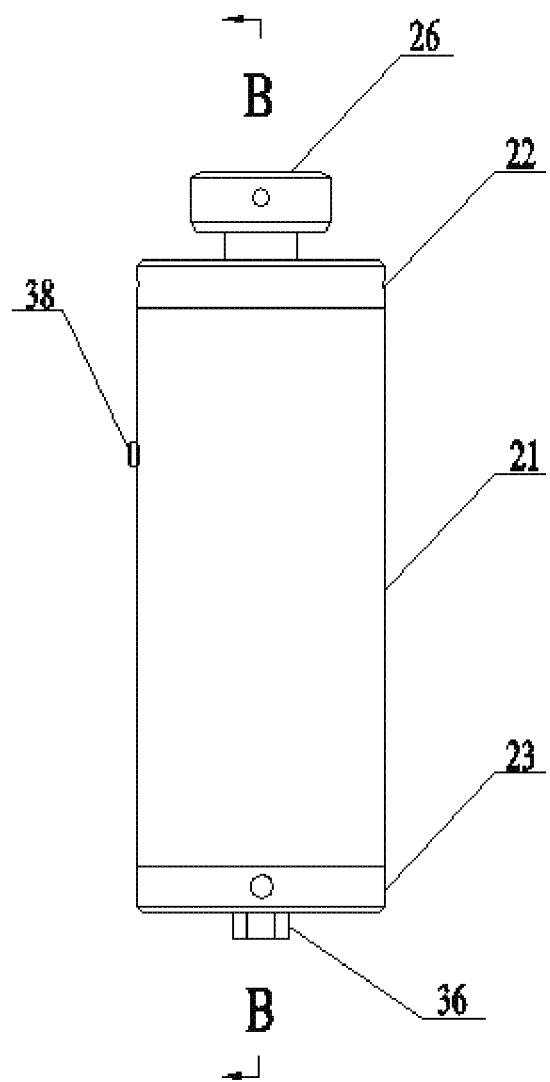
FIG. 6 is a side view of the crack simulation experiment instrument according to Embodiment 1 of the present disclosure.
Figure 7:
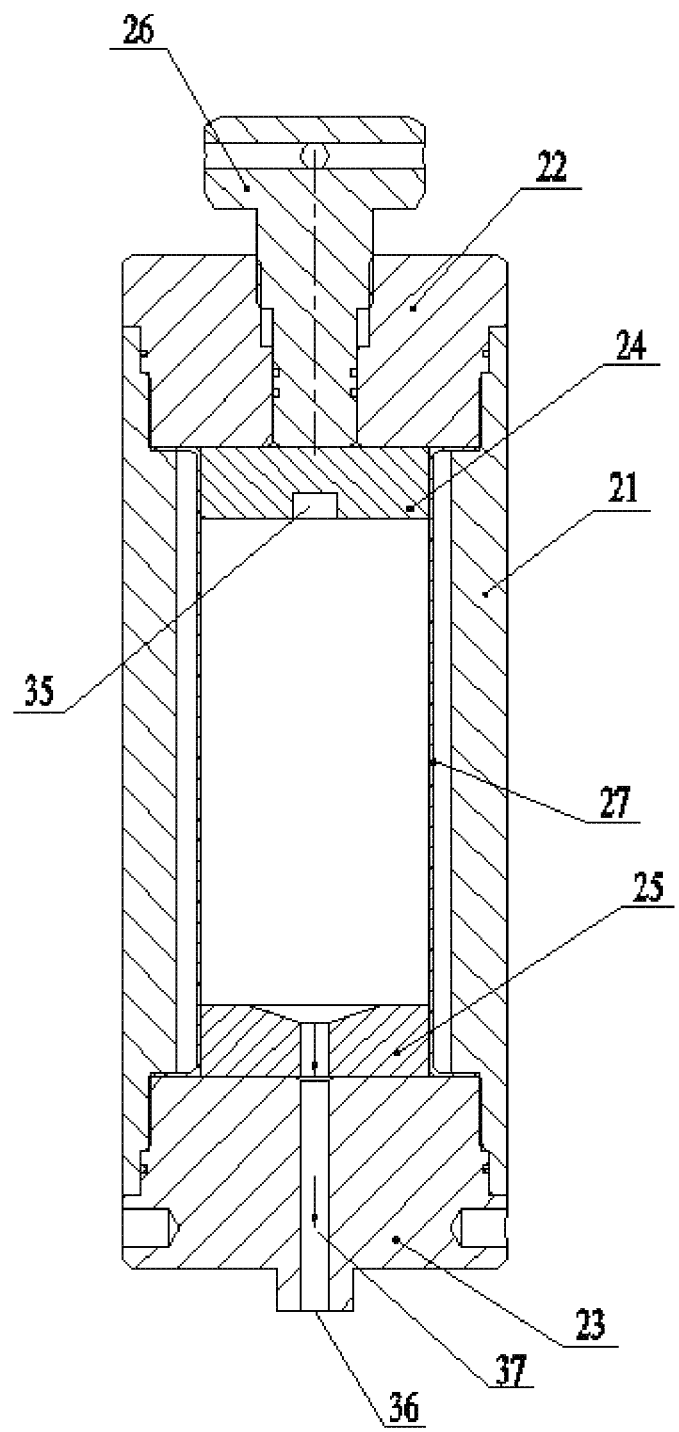
FIG. 7 is a cross-sectional view along B-B in FIG. 6.

Referring to FIG. 1, the experiment device includes a crack simulation experiment instrument 1, a crack simulation experiment instrument fixing device 2, a fluid reservoir tank 3, a recycle pool 4, a hydraulic pump 5, a hand pump 6, a fluid weighting electronic balance 7, an inlet pressure gauge 8, an outlet pressure gauge 9, a first back pressure valve 10, and a second back pressure valve 400.

A fluid outlet of the fluid reservoir tank 3 is communicated with a fluid inlet of the hydraulic pump 5 through a pipeline, and a fluid outlet of the hydraulic pump 5 is communicated with a fluid inlet 31 of the crack simulation instrument 1 through an input pipeline 310;

The inlet pressure gauge 8 is provided on the input pipeline 310;

A fluid outlet 32 of the crack simulation experiment instrument 1 is connected to upright an upper part of the recycle pool 4 through an output pipeline 320, and a fluid outlet of the output pipeline 320 is provided with the first back pressure valve 10;

The outlet pressure gauge 9 is provided on the output pipeline 320;

A drain pipe is provided in a fluid seepage port 36, and the second back pressure valve 400 is provided on the drain pipe;

The fluid weighing electronic balance 7 is provided with a fluid weighing container which is arranged upright below an outlet of the drain pipe. The fluid weighing electronic balance 7 is configured to collect and weigh the fluid that enters the drain pipe from the fluid seepage port 36 and then flows out of the outlet of the drain pipe;

The hand pump 6 is communicated with an air inlet 38 provided on a side wall of a cylinder body 21.

When the hand pump 6 supplies a pressure to a annular space formed between a rubber sleeve 27 and the cylinder body 21, due to deformability of the rubber sleeve 27, the pressure input by the hand pump 6 can smoothly transfer to a rock-mass sample 11 to enable a radial pressure to be applied on the rock-mass sample 11.

Referring to FIGS. 2 to 7, the crack simulation experiment instrument 1 includes the cylinder body 21, an upper cover 22, a lower cover 23, an upper plug 24, a lower plug 25, an indenter 26, the rubber sleeve 27 and a sealing ring 28.

The upper cover 22 and the lower cover 23 are arranged at top and bottom ends of the cylinder body 21, respectively. The upper plug 24 and the lower plug 25 are arranged inside the cylinder body 21 and closely attached to the upper cover 22 and the lower cover 23, respectively. The upper plug 24, the lower plug 25 and the cylinder body 21 jointly enclose an accommodating cavity 20, a geometric size of which can properly accommodate the rock-mass sample 11, and a dynamic crack simulation mechanism is installed inside the accommodating cavity 20.

Figure 8:
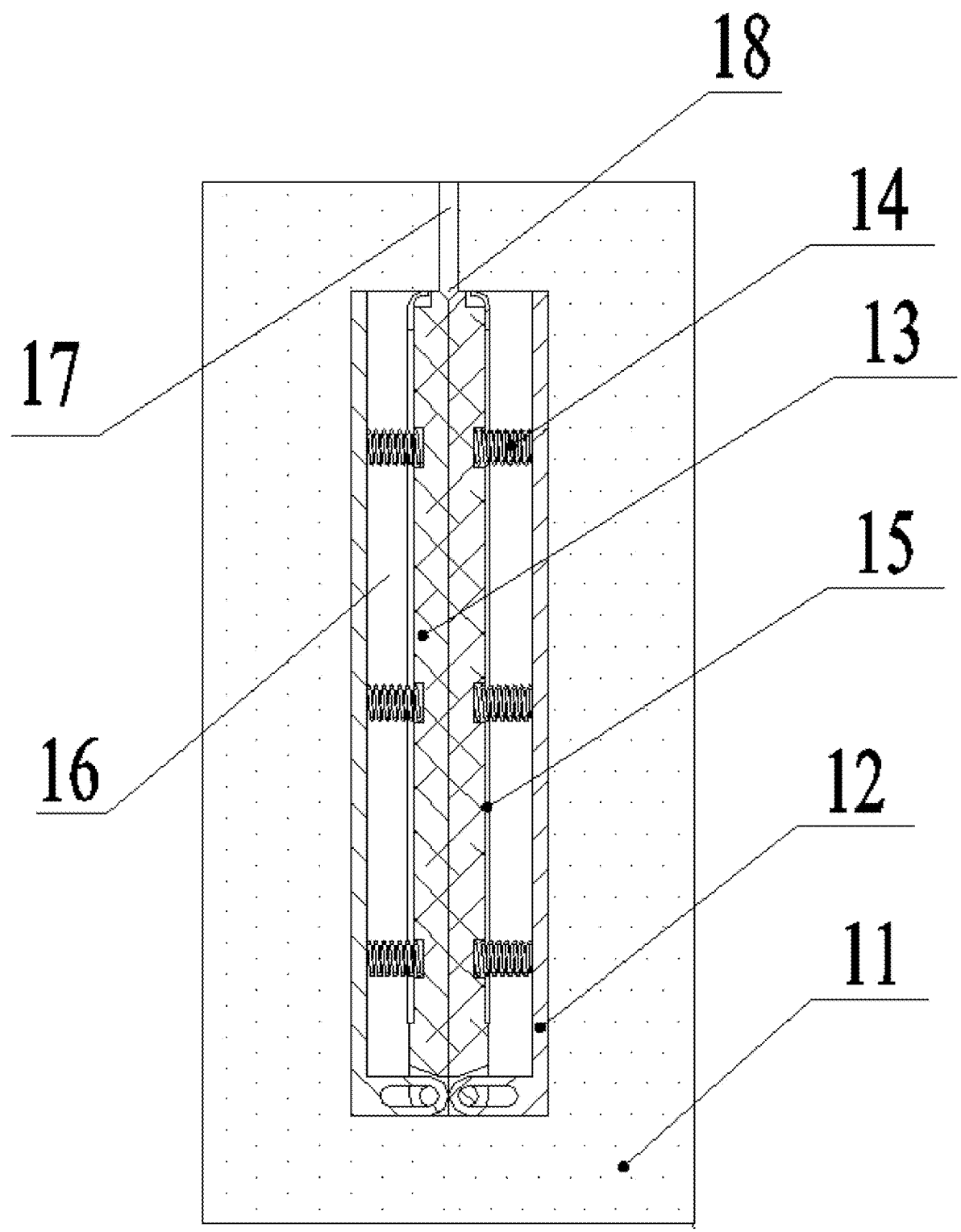
FIG. 8 is a longitudinal cross-sectional view of the dynamic crack simulation mechanism according to Embodiment 1 of the present disclosure.

Referring to FIG. 8, the dynamic crack simulation mechanism can dynamically simulate morphology change of a mud shale crack, and includes a rock-mass sample 11, a fixed plate 12, two seam plates 13, multiple sets of springs 14, and a sealing rubber sleeve 15.

In this case, the rock-mass sample 11 is a mud shale sample in which a hollow groove 16 is provided inside, and an upper part of the hollow groove 16 is communicated with a fluid inlet channel 17 of the dynamic crack simulation mechanism;

The fixing plate 12 is fixed on the side wall and a bottom of the hollow groove 16;

The two seam plates 13 are arranged symmetrically with respect to the center line of the hollow groove 16. Bottom ends of the two seam plates 13 are both pivotally connected to the fixing plate 12 arranged at the bottom of the hollow groove 16, and top ends of the two seam plates 13 both touch a top surface of the hollow groove 16. When the two seam plates 13 are in a closed state, the top ends of the two seam plates 13 splice with each other to just form an inverted corner 18;

The sealing rubber sleeve 15 is laid on outer surfaces of the seam plates 13. The sealing rubber sleeve 15 extends, from bottom to top, from the bottom ends of the seam plates 13 to contact points between the top ends of the seam plates 13 and the top surface of the hollow groove 16, so as to enable complete sealing of the seam plates 13 from the rock-mass sample 11;

Several sets of springs 14 are arranged between the seam plates 13 and the fixing plate 12 arranged at the side wall of the hollow groove 16. Each set of springs 14 includes two springs 14 located at the same height. Ends of each spring 14 are respectively fixed on the sealing rubber sleeve 15 and the fixed plate 12. A difficulty level that an aperture-gap cracks can be simulated by adjusting an elastic coefficient of the springs 14.

After leaking stoppage slurry enters the hollow groove 16 of the rock-mass sample 11 from the fluid inlet channel 17 of the dynamic crack simulation mechanism, the leaking stoppage slurry enters the inverted corner 18 at the top ends of the two seam plates 13 and expands the two seam plates 13 apart from each other to rotate to both sides around the fixed plate 12, so as to dynamically simulate an aperture-gap cracking process.

As a specific implementation, the several sets of springs 14 are arranged symmetrically about the center line of the hollow groove 16.

Figure 9:
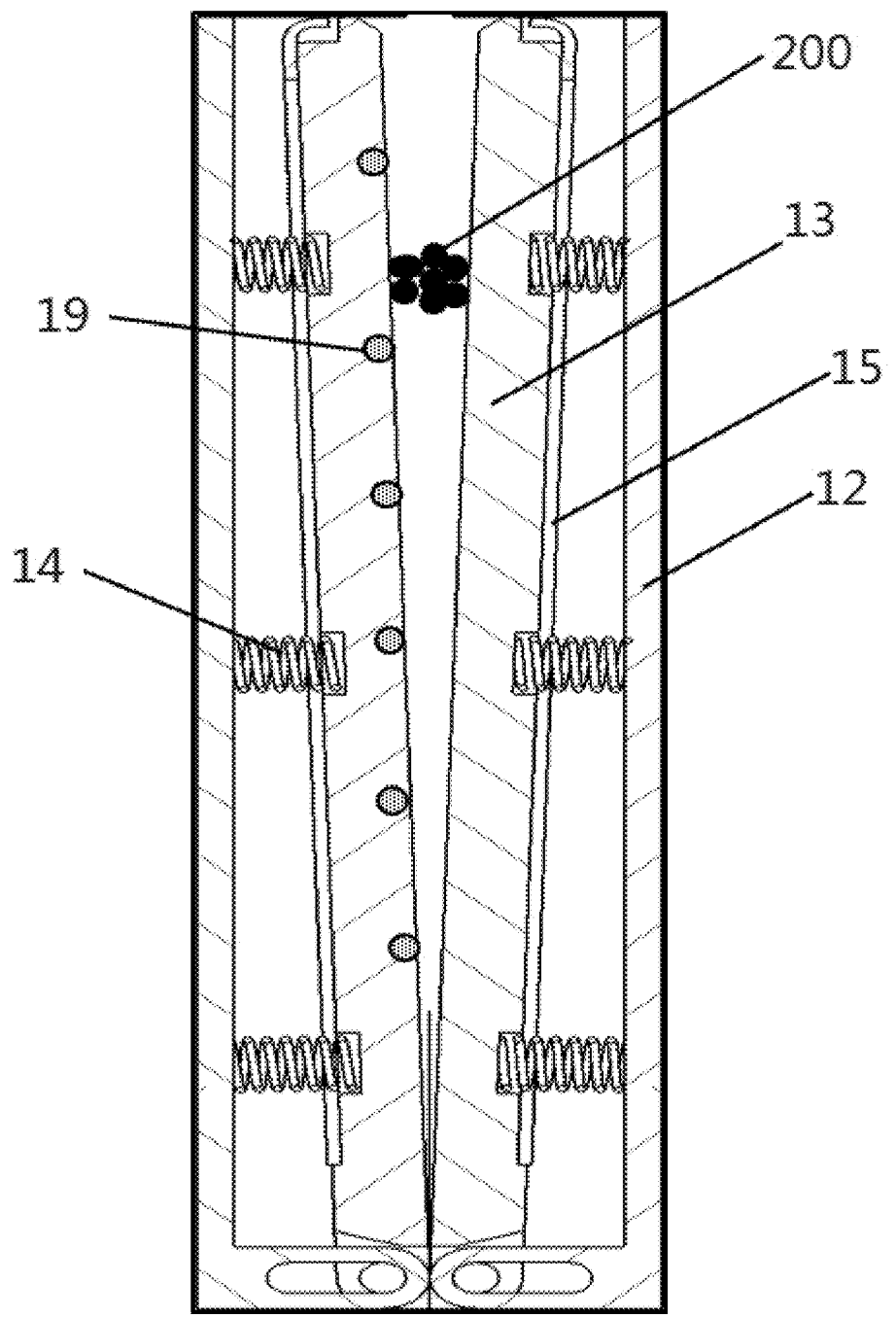
FIG. 9 is a longitudinal cross-sectional view of inside of a hollow groove of the dynamic crack simulation mechanism according to Embodiment 1 of the present disclosure.

Referring to FIG. 9, in order to enable real-time determination of leaking stoppage location and leaking stoppage speed, one of the seam plates 13 is provided with a plurality of pressure measuring points at intervals, each pressure measuring point is provided with a pressure sensor 19 which extends to the outside through a wire and is provided with a pressure sensor connector.

Preferably, the number of pressure measuring points is 4 to 6.

Referring back to FIGS. 2 to 7, a fluid inlet 31 and a fluid outlet 32 are, respectively, provided on both sides of the upper cover 22. A fluid inlet channel slot 33 is provided between the fluid inlet 31 and the accommodating cavity 20, and the fluid inlet channel slot 33 sequentially passes through, from outside to inside, the upper cover 22 and the upper plug 24 that are on the side close to the fluid inlet 31. A fluid outlet channel slot 34 is provided between the fluid outlet 32 and the accommodating cavity 20, and the fluid outlet channel slot 34 sequentially passes through, from inside to outside, the upper plug 24 and the upper cover 22 that are on the side close to the fluid outlet 32. A junction slot 35 is provided between the fluid inlet channel slot 33 and the fluid outlet channel slot 34 of the upper plug 24, and the junction slot 35 is communicated with the accommodating cavity 20.

Further, the fluid seepage port 36 is provided at a bottom of the lower cover 23. A fluid seepage channel 37 is provided between the fluid seepage port 36 and the accommodating cavity 20, and the fluid seepage channel 37 sequentially penetrates middle parts of the lower plug 25 and the lower cover 23.

Further, the center lines of the fluid inlet channel slot 33 and the fluid outlet channel slot 34 are located on the same line, and a line connecting the fluid inlet channel slot 33 and the fluid outlet channel slot 34 is communicated with the junction slot 35 in a cross-shape pattern.

In order to ensure sealing performance of the accommodating cavity 20, a sealing ring 28 is provided between an upper part of the cylinder body 21 and the upper cover 22.

In order to further improve the sealing performance of the accommodating cavity 20, a rubber sleeve 27 is provided at inner wall of the cylinder body 21 and at connections between the cylinder body 21 and the upper plug 24, the lower plug 25. The rubber sleeve 27 divides the cylinder body 21 into two closed spaces, that are, respectively, an annular space formed between the rubber sleeve 27 and the cylinder body 21 and a space enclosed by the rubber sleeve 27, the upper plug 24 and the lower plug 25. In this case, the upper plug 24 and the lower plug 25 are both rubber plugs.

Further, an indenter 26 is provided on the upper cover 22 in a threaded connection. Specifically, the upper cover 22 is provided with a groove, inner wall of the groove is provided with inner thread, and the indenter 26 is provided with outer thread. In the process of tightly screwing the indenter 26 onto the groove of the upper cover 22, the indenter 26 acts on the upper plug to exert a force to the rock-mass sample 11, so as to enable change of an axial stress to the rock-mass sample 11.

Further, the cylinder body 21 is provided with through holes for arranging pressure sensor connectors of the pressure sensors 19 in a penetrating manner. A wire connecting a pressure sensor 19 and a pressure sensor connector is arranged to pass through a rubber plug which is provided in a through hole in a sealed manner.

Figure 10:
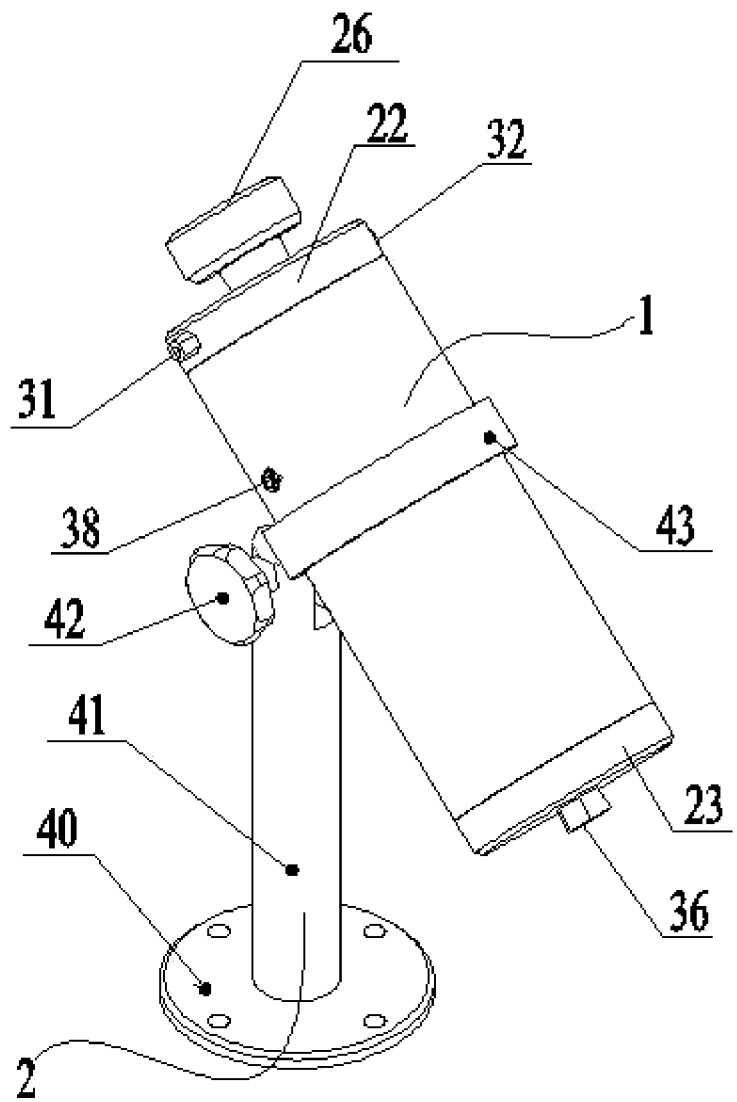
FIG. 10 is a schematic diagram of the crack simulation experiment instrument installed on a fixing device according to Embodiment 1 of the present disclosure.

Referring to FIG. 10, the crack simulation experiment instrument fixing device 2 includes a base 40, a support rod 41, a steel collar 43 and a screwing knob 42. In this case, the support rod 41 is fixed on the base 40. An outer shape of the crack simulation experiment instrument 1 is a cylinder. The steel collar 43 includes a ring part and a rod part, and the ring part of the steel collar 43 is sleeved on the outside of the crack simulation instrument 1. The screwing knob 42 includes a fixedly connected screw part and a knob part, and outer wall of the screw part of the screwing knob 42 is provided with outer thread. A top end of the support rod 41 is provided with a hinge ring, and top side wall of the support rod 41 is provided with an inner threaded hole. The rod part of the steel collar 43 is hinged to the support rod 41. The screw part of the screwing knob 42 is arranged inside the threaded hole on the top side wall of the support rod 41 and is fixedly connected to the rod part of the steel collar 43. Tightening of the screwing knob 42 can implement adjustment and fixing of an angle of the crack simulation experiment instrument 1.

Embodiment 2

Provided in Embodiment 2 is an experiment method for obtaining crack dynamic changes of a crack plugged with fluid medium, in which the dynamic crack leaking stoppage evaluation experiment device of Embodiment 1 is used and a method for obtaining the dynamic change process of a crack by plugging the crack with clean water or leaking stoppage slurry to promote dynamic changes of the crack is used. The experiment method specifically includes the following steps A to D:

Step A, assembling a crack simulation instrument 1, which includes the following Steps A1 to A3:

Step A1, the rock-mass sample 11, the fixed plate 12, the two seam plates 13, the multiple sets of springs 14, and the sealing rubber sleeve 15 are assembled into a dynamic crack simulation mechanism;

Step A2, the lower plug 25, the dynamic crack simulation mechanism, and the upper plug 24 are installed within the rubber sleeve 27 in sequence to assemble a crack simulation instrument 1; and Step A3, the upper cover 22 and the lower cover 23 are turned to make the rock-mass sample 11 generate an axial stress;

Step B, sealing the accommodating cavity 20, and setting valve values of the first back pressure valve 10 and the second back pressure valve 400 and a flow rate of the hydraulic pump 5, which includes the following Steps B1 to B2:

Step B1, the hand pump 6 is activated to inject gas into an air inlet 38 on the side wall of the cylinder body 21 until a confining pressure of 10 MPa is formed within an annular space formed between the cylinder body 21 and the rubber sleeve 27, so that sealing of the accommodating cavity 20 enclosed by the rock-mass sample 11, the upper plug 24 and the lower plug 25 is formed; and Step B2, a valve value of the first back pressure valve 10 is set to 4.5 MPa, a valve value of the second back pressure valve 400 is set to 1.5 MPa, and a flow rate of the hydraulic pump 5 is set to 2 L/min;

Step C, plugging a crack with clean water or leaking stoppage slurry to obtain dynamic change process of the crack;

In this case, said plugging a crack with clean water to obtain dynamic change process of the crack specifically includes the following steps C11 to C13:

Step C11, the hydraulic pump 5 is activated so that clean water enters, via the fluid inlet 31, the crack simulation experiment instrument 1 successively through the fluid reservoir tank 3, the hydraulic pump 5, and the input pipeline 310 in sequence. A portion of the clean water enters the crack by passing through the fluid inlet channel slot 33, the junction slot 35, and the fluid inlet channel 17 and the inverted corner 18 of the crack simulation mechanism, and then reaches the second back pressure valve 400 by passing through the fluid seepage channel 37 and the fluid seepage port 36. The other portion of the clean water reaches the first back pressure valve 10 by passing through the fluid outlet channel slot 34, the fluid outlet 32 and the output pipeline 320;

Step C12, the injected clean water gradually forms a hydraulic pressure at the fluid inlet channel 17 and the inverted corner 18; and Step C13, when the hydraulic pressure exceeds an elastic force of the springs 14, the two seam plates 13 are gradually expanded apart from each other. As the hydraulic pressure at the fluid inlet channel 17 and the inverted corner 18 increases, an opening degree of a crack formed by expanding the two seam plates 13 increases gradually until the hydraulic pressure exceeds a pressure value of 1.5 MPa set for the second back pressure valve 400, then the opening degree of the crack formed by the two seam plates 13 would not change any longer.

Through these above steps, control of the opening degree of the two seam plates 13 can be achieved by configuring a pressure value of the second back pressure valve 400, so as to enable a dynamic crack simulation process.

In addition, said plugging a crack with leaking stoppage slurry to obtain dynamic change process of the crack specifically includes the following steps C21 to C26:

Step C21, the reservoir tank 3 is filled with leaking stoppage slurry;

Step C22, the hydraulic pump 5 is activated, so that the leaking stoppage slurry in the reservoir tank 3 enters, via the fluid inlet 31, the crack simulation instrument 1 through the hydraulic pump 5 and the input pipeline 310. A portion of the leaking stoppage slurry enters a crack by passing through the fluid inlet channel slot 33, the junction slot 35, and the fluid inlet channel 17 and the inverted corner 18 of the crack simulation mechanism, and then reaches the second back pressure valve 400 by passing through the fluid seepage channel 37 and the seepage port 36. The other portion of the leaking stoppage slurry reaches the first back pressure valve 10 by passing through the fluid outlet channel slot 34, the fluid outlet 32 and the output pipeline 320;

Step C23, the leaking stoppage slurry gradually accumulates within the inverted corner 18 to form a hydraulic pressure;

Step C24, when the hydraulic pressure at the inverted corner 18 exceeds an elastic force of the springs 14, the two seam plates 13 are gradually expanded apart from each other. As the hydraulic pressure inside the crack simulation mechanism increases, an opening degree of the crack expanded by the two seam plates 13 gradually increases until the hydraulic pressure exceeds a pressure value of 1.5 MPa set for the second back pressure valve 400, then the opening degree of the crack formed by the two seam plates 13 would not change any longer; at the same time, particles in the leaking stoppage slurry form a leaking stoppage layer 200 in a channel of the crack;

Step C25, the leaking stoppage slurry is continuously injected into the fluid inlet channel 17 and the inverted corner 18 to form a hydraulic pressure, and the hydraulic pressure increases gradually. Under the action of the hydraulic pressure, the two seam plates 13 are further expanded apart, so that the leaking stoppage layer 200 is damaged or a location of the leaking stoppage layer 200 is transferred, and a second leaking stoppage layer is newly formed; and Step C26, change of a pressure value of the pressure sensor 19 is recorded as a function of time, when it is observed that the pressure value of the pressure sensor 19 changes suddenly, and a position of a pressure measurement point on the seam plate 13 that corresponds to the pressure sensor 19 is recorded to determine leaking stoppage location of the leaking stoppage slurry in the crack.

The foregoing steps are mainly used to simulate a leaking stoppage process in case of a dynamic crack and evaluate a variation range of the opening degree of the crack plugged by the leaking stoppage material. Leaking stoppage ability of the leaking stoppage material working on the dynamic crack can be quantitatively evaluated by means of a relationship of the pressure value of each pressure measurement point varying as a function of time.

Step D, evaluating dynamic crack leaking stoppage effect.

Evaluation on the dynamic crack leaking stoppage effect includes quantitative evaluation on leaking stoppage location and dynamic pressure bearing capacity of the leaking stoppage slurry under scouring action of the leaking stoppage slurry, evaluation on an effect of fluid rheological parameters on stability of the second leaking stoppage layer after circulating fluid is replaced in the subsequent well drilling process, and evaluation on an effect of hydraulic parameters of the leaking stoppage slurry on the stability of the second leaking stoppage layer.

In this case, the quantitative evaluation on leaking stoppage location and dynamic pressure bearing capacity of the leaking stoppage slurry under scouring action of the leaking stoppage slurry is implemented after plugging the crack with the leaking stoppage slurry to obtain dynamic change process of the crack, and specifically includes the following steps X1 to X5:

Step X1, after a stable second leaking stoppage layer is formed, a pressure value of the first back pressure valve 10 is adjusted to be equal to a value of the inlet pressure gauge 8;

Step X2, the excess leaking stoppage slurry will enter the waste fluid pool 4 (the recycle pool) through the first back pressure valve 10, so that the leaking stoppage slurry inside the fluid inlet channel 17 and the inverted corner 18 of the crack simulation mechanism forms a dynamic flow, which will cause continuous scour flow onto the leaking stoppage layer 200 until the second leaking stoppage layer is damaged;

Step X3, the second leaking stoppage layer is gradually damaged, so that the value of the inlet pressure gauge 8 is varied and a width of the crack decreases;

Step X4, once a pressure at the fluid inlet channel 17 and the inverted corner 18 of the crack simulation mechanism is lower than the pressure value of the first back pressure valve 10, the leaking stoppage slurry stops dynamic flowing and plugs the crack once again, and the steps X2 to X3 are repeated then; and Step X5, change of a pressure value of the pressure sensor 19 is recorded as a function of time, when it is observed that the pressure value of the pressure sensor 19 changes suddenly, a position of a pressure measurement point on the seam plate 13 that corresponds to the pressure sensor 19 is recorded to determine leaking stoppage location of the leaking stoppage slurry in the crack.

By analyzing a relationship of the pressure value of each pressure measurement point varying as a function of time, the relationship is used to perform quantitative evaluation on the leaking stoppage location and the dynamic pressure bearing capacity of the leaking stoppage slurry working on the dynamic crack under an impact of scouring action of the leaking stoppage slurry.

The evaluation on an effect of fluid rheological parameters on stability of the second leaking stoppage layer after circulating fluid is replaced in the subsequent well drilling process is implemented after plugging the crack with the leaking stoppage slurry to obtain dynamic change process of the crack, and specifically includes:

Step Y, after a stable second leaking stoppage layer is formed, the hydraulic pump 5 is stopped, the leaking stoppage slurry is replaced with clean water, water-based well drilling fluid or oil-based well drilling fluid, and the pressure value of the first back pressure valve 10 is adjusted to be equal to a value of the inlet pressure gauge 8 that is before stopping the pump.

This approach is used to simulate a viscosity of circulating fluid, and carries out study on an effect on stability of the second leaking stoppage layer inside the dynamic crack, which is mainly used to evaluate the effect of rheological parameters, such as the viscosity of the fluid, on the stability of the second leaking stoppage layer after the circulating fluid is replaced in the subsequent well drilling process.

The evaluation on an effect of hydraulic parameters on stability of the leaking stoppage slurry of the second leaking stoppage layer is implemented after plugging the crack with the leaking stoppage slurry to obtain dynamic change process of the crack, and specifically includes:

Step Z1, after a stable second leaking stoppage layer is formed, the pressure value of the first back pressure valve 10 is adjusted to be equal to a value of the inlet pressure gauge 8, the excess leaking stoppage slurry will enter the waste fluid pool 4 through the first back pressure valve 10, so that the leakage leaking stoppage slurry inside the fluid inlet channel 17 and the inverted corner 18 of the crack simulation mechanism form a dynamic flow;

Step Z2, a flow rate of the hydraulic pump 5 is increased to 3 L/min and is kept for 1 h;

Step Z3, the flow rate of the hydraulic pump 5 is increased to 4 L/min, and is still kept for 1 h;

Step Z4, the flow rate of the hydraulic pump 5 is increased with an increment of 1 L/min per hour until the leakage stoppage layer 200 is damaged;

Step Z5, change of the pressure value of the pressure sensor 19 is recoded as an function of time, when it is observed that the pressure value of the pressure sensor 19 changes suddenly, a position of a pressure measurement point on the seam plate 13 that corresponds to the pressure sensor 19 is recorded to determine leaking stoppage location of the leaking stoppage slurry in the crack; and Step Z6, a curve is plotted regarding a relationship between the pressure value of the pressure measuring point on the seam plate 13 and the flow rate.

This approach is mainly used to evaluate the effect of hydraulic parameters of the leaking stoppage slurry on stability of the second leaking stoppage layer, wherein the hydraulic parameters include flow rate, displacement, etc.

Although the present disclosure has been described in detail with general descriptions and specific embodiments above, it is apparent to those skilled in the art that some modifications or improvements can be implemented on the basis of the present disclosure. Therefore, all these modifications or improvements implemented without departing from the spirit of the present disclosure fall into the scope of the present disclosure.

INDUSTRIAL APPLICATION

The present disclosure has the following advantages by adopting the foregoing technical solutions: in the dynamic crack leaking stoppage evaluation experiment device and the experiment method thereof disclosed by the present disclosure, when leaking stoppage slurry enters the hollow groove of a rock-mass sample from the fluid inlet channel of the dynamic crack simulation mechanism, the leaking stoppage slurry enters the inverted corners at the top ends of the two seam plates, and the two seam plates are expanded apart from each other to rotate to both sides around the fixed plate, thereby dynamically simulating an aperture-gap cracking process. At the same time, the leaking stoppage slurry enters the crack to plug the crack and form a leaking stoppage layer, as a result which a pressure at entrance of the crack increases, the seam plates would be further expanded apart under the action of the increased pressure, and a second leaking stoppage layer is formed, thereby implementing a dynamic crack leaking stoppage experiment. The dynamic crack leaking stoppage evaluation experiment device disclosed by the present disclosure can simulate a dynamic change process of a crack from a closed state to an open state, and the experiment method can be applied to study on a variation range of the width of the crack that have been subjected to self-adaptive leaking stoppage with various combinations of leaking stoppage materials and under different increments, and it can also be applied to quantitatively study on effecting patterns of rheological parameters and hydraulic parameters of well drilling fluid on stability of a leaking stoppage layer in the dynamic crack, so that enabled is not only simulation of leaking stoppage process of a dynamic crack, but also real-time monitoring and evaluation on leaking stoppage effect and leaking stoppage location inside the dynamic crack.

The invention claimed is:

1. A dynamic crack leaking stoppage evaluation experiment device, characterized in that, the device comprises a crack simulation experiment instrument (1), a fluid reservoir tank (3), a recycle pool (4), a hydraulic pump (5), and a hand pump (6), a fluid weighting electronic balance (7), an inlet pressure gauge (8), an outlet pressure gauge (9), a first back pressure valve (10), and a second back pressure valve (400), an upper part of the crack simulation instrument (1) is provided with a fluid inlet (31) and a fluid outlet (32), and a bottom of the crack simulation instrument (1) is provided with a fluid seepage port (36);

a fluid outlet of the fluid reservoir tank (3) is communicated with a fluid inlet of the hydraulic pump (5) through a pipeline, and a fluid outlet of the hydraulic pump (5) is communicated with the fluid inlet of the crack simulation instrument (1) through an input pipeline (310);

the inlet pressure gauge (8) is provided on the input pipeline (310);

a fluid outlet (32) of the crack simulation experiment instrument (1) is connected to upright an upper part of the recycle pool (4) through an output pipeline (320), and the fluid outlet end of the output pipeline (320) is provided with the first back pressure valve (10);

the outlet pressure gauge (9) is provided on the output pipeline (320);

the fluid seepage port (36) is provided with a drain pipe, on which the second back pressure valve (400) is provided;

the fluid weighing electronic balance (7) is provided with a fluid weighing container which is arranged upright below an outlet of the drain pipe;

the hand pump (6) is communicated with an air inlet (38) provided on a side wall of a cylinder body (21);

when the hand pump (6) supplies a pressure to an annular space formed between a rubber sleeve (27) and the cylinder body (21), due to deformability of the rubber sleeve (27), the pressure input by the hand pump (6) can smoothly transfer to a rock-mass sample (11) to enable a radial pressure to be applied on the rock-mass sample (11).

2. The dynamic crack leaking stoppage evaluation experiment device according to claim 1, characterized in that, the crack simulation experiment instrument (1) comprises the cylinder body (21), an upper cover (22), a lower cover (23), an upper plug (24), a lower plug (25), an indenter (26), and the rubber sleeve (27), the upper cover (22) and the lower cover (23) are arranged at top and bottom ends of the cylinder body (21), respectively, the upper plug (24) and the lower plug

(25) are arranged inside the cylinder body (21) and closely attached to the upper cover (22) and the lower cover (23), respectively; the upper plug (24), the lower plug (25) and the cylinder body (21) jointly enclose an accommodating cavity (20), a geometric size of the accommodating cavity (20) can properly accommodate the rock-mass sample (11);

the fluid inlet (31) and the fluid outlet (32) are provided on both sides of the upper cover (22), respectively, a fluid inlet channel slot (33) is provided between the fluid inlet (31) and the accommodating cavity (20), and the fluid inlet channel slot (33) sequentially passes through, from outside to inside, the upper cover (22) and the upper plug (24) that are on the side close to the fluid inlet (31);

a fluid outlet channel slot (34) is provided between the fluid outlet (32) and the accommodating cavity (20), and the fluid outlet channel slot (34) sequentially passes through, from inside to outside, the upper plug (24) and the upper cover (22) that are on the side close to the fluid outlet (32);

a junction slot (35) is provided between the fluid inlet channel slot (33) and the fluid outlet channel slot (34) of the upper plug (24), and the junction slot (35) is communicated with the accommodating cavity (20).

3. The dynamic crack leaking stoppage evaluation experiment device according to claim 2, characterized in that, the crack simulation experiment instrument (1) is equipped with a dynamic crack simulation mechanism, the dynamic crack simulation mechanism comprises the rock-mass sample (11), a fixed plate (12), two seam plates (13), multiple sets of springs (14), and a sealing rubber sleeve (15), the rock-mass sample (11) is provided with a hollow groove (16) inside, an upper part of the hollow groove (16) is communicated with a fluid inlet channel (17) of the dynamic crack simulation mechanism;

the fixing plate (12) is fixed on a side wall and a bottom of the hollow groove (16);

the two seam plates (13) are arranged symmetrically with respect to a center line of the hollow groove (16), bottom ends of the two seam plates (13) are both pivotally connected to the fixing plate (12) arranged at the bottom of the hollow groove (16), and top ends of the two seam plates (13) both touch a top surface of the hollow groove (16); when the two seam plates (13) are in a closed state, the top ends of the two seam plates (13) splice with each other to form an inverted corner (18);

the sealing rubber sleeve (15) is laid on outer surfaces of the seam plates (13); the sealing rubber sleeve (15) extends, from bottom to top, from the bottom ends of the seam plates (13) to contact points between the top ends of the seam plates (13) and the top surface of the hollow groove (16), so as to enable complete sealing of the seam plates (13) from the rock-mass sample (11);

center lines of the fluid inlet channel slot (33) and the fluid outlet channel slot (34) are located on one same line, and a line connecting the fluid inlet channel slot (33) and the fluid outlet channel slot (34) is communicated with the junction slot (35) in a cross-shape pattern;

the fluid seepage port (36) is provided at a bottom of the lower cover (23), a fluid seepage channel (37) is provided between the fluid seepage port (36) and the accommodating cavity (20), and the fluid seepage channel (37) sequentially penetrates middle parts of the lower plug (25) and the lower cover (23);

the multiple sets of springs (14) are arranged, at intervals, between the seam plates (13) and the fixing plate (12) arranged at the side wall of the hollow groove (16), each set of springs (14) includes two springs (14) located at an identical height, and ends of each spring (14) are respectively fixed on the sealing rubber sleeve (15) and the fixed plate (12);

one of the seam plates (13) is provided with a plurality of pressure measuring points at intervals, and each pressure measuring point is provided with a pressure sensor (19) which extends to outside through a wire and is provided with a pressure sensor connector, wherein the dynamic crack simulation mechanism is configured in such a way that after leaking stoppage slurry enters the hollow groove (16) of the rock-mass sample (11) from the fluid inlet channel (17) of the dynamic crack simulation mechanism, the leaking stoppage slurry enters the inverted corner (13) at the top ends of the two seam plates (13) and expands the two seam plates (13) apart from each other to rotate to both sides around the fixed plate (12), so as to dynamically simulate an aperture-gap cracking process.

4. The dynamic crack leaking stoppage evaluation experiment device according to claim 3, characterized in that, the rubber sleeve (27) is provided at an inner wall of the cylinder body (21) and at connections between the cylinder body (21) and the upper plug (24), the lower plug (25); the rubber sleeve (27) divides the cylinder body (21) into two closed spaces, that are, respectively, an annular space formed between the rubber sleeve (27) and the cylinder body (21) and a space enclosed by the rubber sleeve (27), the upper plug (24) and the lower plug (25);

the air inlet (38) is provided on the side wall of the cylinder body (21), and the air inlet (38) is communicated with the annular space formed between the rubber sleeve (27) and the cylinder body (21).

5. An experiment method for obtaining crack dynamic changes of a crack plugged with fluid medium, comprising the dynamic crack leaking stoppage evaluation experiment device according to claim 4, characterized in that, the method comprises steps of:

Step A, assembling the crack simulation instrument (1);

Step A1, assembling the rock-mass sample (11), the fixed plate (12), the two seam plates (13), the multiple sets of springs (14), and the sealing rubber sleeve (15) into the dynamic crack simulation mechanism;

Step A2, installing the lower plug (25), the dynamic crack simulation mechanism, and the upper plug (27) inside the rubber sleeve (27) in sequence to assemble them into the crack simulation instrument (1); and Step A3, turning the upper cover (22) and the lower cover (23) to make the rock-mass sample (11) generate an axial stress;

Step B, sealing the accommodating cavity (20), and setting valve values of the first back pressure valve (10) and the second back pressure valve (400) and a flow rate of the hydraulic pump (5);

Step C, plugging a crack with clean water or leaking stoppage slurry to obtain dynamic change process of the crack; and Step D, evaluating dynamic crack leaking stoppage effect, wherein evaluation on the dynamic crack leaking stoppage effect includes quantitative evaluation on leaking stoppage location and dynamic pressure bearing capacity of the leaking stoppage slurry under scouring action of the leaking stoppage slurry, evaluation on an effect of fluid rheological parameters on stability of the second leaking stoppage layer after circulating fluid is replaced in the subsequent well drilling process, and evaluation on an effect of hydraulic parameters of the leaking stoppage slurry on the stability of the second leaking stoppage layer.

6. The experiment method according to claim 5, characterized in that,
plugging a crack with clean water to obtain dynamic change process of the crack specifically comprises steps of:
Step C11, activating the hydraulic pump (5) so that clean water enters, via the fluid inlet (31), the crack simulation experiment instrument (1) successively through the fluid reservoir tank (3), the hydraulic pump (5), and the input pipeline (310) in sequence, wherein a portion of the clean water enters the crack by passing through the fluid inlet channel slot (33), the junction slot (35), and the fluid inlet channel (17) and the inverted corner (18) of the crack simulation mechanism, and then reaches the second back pressure valve (400) by passing through the fluid seepage channel (37) and the fluid seepage port (36); and the other portion of the clean water reaches the first back pressure valve (10) by passing through the fluid outlet channel slot (34), the fluid outlet (32) and the output pipeline (320);
Step C12, forming, by the injected clean water, a hydraulic pressure gradually at the fluid inlet channel (17) and the inverted corner (18); and
Step C13, expanding, when the hydraulic pressure exceeds an elastic force of the springs (14), the two seam plates (13) apart from each other gradually, wherein as the hydraulic pressure at the fluid inlet channel (17) and the inverted corner (18) increases, an opening degree of the crack formed by expanding the two seam plates (13) increases gradually until the hydraulic pressure exceeds a pressure value of 1.5 MPa set for the second back pressure valve (400), then the opening degree of the crack formed by the two seam plates (13) changes no longer.

7. The experiment method according to claim 5, characterized in that,
plugging a crack with leaking stoppage slurry to obtain dynamic change process of the crack specifically comprises steps of:
Step C21, filling the reservoir tank (3) with leaking stoppage slurry;
Step C22, activating the hydraulic pump (5) so that the leaking stoppage slurry in the reservoir tank (3) enters, via the fluid inlet (31), the crack simulation instrument (1) through the hydraulic pump (5) and the input pipeline (310), wherein a portion of the leaking stoppage slurry enters the crack by passing through the fluid inlet channel slot (33), the junction slot (35), and the fluid inlet channel slot (17) and the inverted corner (18) of the crack simulation mechanism, and then reaches the second back pressure valve (400) by passing through the fluid seepage channel (37) and the seepage port (36); and the other portion of the leaking stoppage slurry reaches the first back pressure valve (10) by passing through the fluid outlet channel slot (34), the fluid outlet (32) and the output pipeline (320);
Step C23, accumulating the leaking stoppage slurry gradually within the inverted corner (18) to form a hydraulic pressure;
Step C24, expanding, when the hydraulic pressure at the inverted corner (18) exceeds an elastic force of the springs (14), the two seam plates (13) apart from each other gradually, wherein as the hydraulic pressure inside the crack simulation mechanism increases, an opening degree of the crack formed by expanding the two seam plates (13) increases gradually until the hydraulic pressure exceeds a pressure value of 1.5 MPa set for the second back pressure valve (400), then the opening degree of the crack formed by the two seam plates (13) changes no longer; at the same time, particles in the leaking stoppage slurry form a leaking stoppage layer (200) in a channel of the crack;
Step C25, injecting the leaking stoppage slurry continuously into the fluid inlet channel (17) and the inverted corner (18) to form a hydraulic pressure which increases gradually, wherein under an action of the hydraulic pressure, the two seam plates (13) are further expanded apart, so that the leaking stoppage layer (200) is damaged or a location of the leaking stoppage layer (200) is transferred, and a second leaking stoppage layer is newly formed; and
Step C26, recording change of a pressure value of the pressure sensor (19) as a function of time, and recording, when it is observed that the pressure value of the pressure sensor (19) changes suddenly, a position of a pressure measurement point on a seam plate (13) that corresponds to the pressure sensor (19) to determine leaking stoppage location of the leaking stoppage slurry in the crack.

8. The experiment method according to claim 5, characterized in that,
the quantitative evaluation on leaking stoppage location and dynamic pressure bearing capacity of the leaking stoppage slurry under scouring action of the leaking stoppage slurry is implemented after plugging the crack with the leaking stoppage slurry to obtain dynamic change process of the crack, and specifically comprises steps of:
Step X1, adjusting, after a stable second leaking stoppage layer is formed, a pressure value of the first back pressure valve (10) to be equal to a value of the inlet pressure gauge (8);
Step X2, leading the excess leaking stoppage slurry into the recycle pool (4) through the first back pressure valve (10), so that the leaking stoppage slurry inside the fluid inlet channel (17) and the inverted corner (18) of the crack simulation mechanism forms a dynamic flow which causes continuous scour flow onto the leaking stoppage layer (200) until the second leaking stoppage layer is damaged;
Step X3, subjecting the second leaking stoppage layer to damage gradually, so that the value of the inlet pressure gauge (8) is varied and a width of the crack decreases;
Step X4, stopping, once a pressure at the fluid inlet channel (17) and the inverted corner (18) of the crack simulation mechanism is lower than the pressure value of the first back pressure valve (10), the leaking stoppage slurry dynamic flowing, plugging the crack once again, and then repeating the Steps X2 to X3; and
Step X5, recording change of a pressure value of the pressure sensor (19) as a function of time, and recording, when it is observed that the pressure value of the pressure sensor (19) changes suddenly, a position of a pressure measurement point on a seam plate (13) that corresponds to the pressure sensor (19) to determine leaking stoppage location of the leaking stoppage slurry in the crack.

9. The experiment method according to claim 5, characterized in that, the evaluation on an effect of fluid rheological parameters on stability of the second leaking stoppage layer after circulating fluid is replaced in the subsequent well drilling process is implemented after plugging the crack with the leaking stoppage slurry to obtain dynamic change process of the crack, and specifically comprises a step of:

Step Y, stopping, after a stable second leaking stoppage layer is formed, the hydraulic pump (5), and replacing the leaking stoppage slurry with clean water, water-based well drilling fluid or oil-based well drilling fluid, and adjusting the pressure value of the first back pressure valve (10) to be equal to a value of the inlet pressure gauge (8) that is before stopping the pump.

10. The experiment method according to claim 5, characterized in that, the evaluation on an effect of hydraulic parameters on stability of the leaking stoppage slurry of the second leaking stoppage layer is implemented after plugging the crack with the leaking stoppage slurry to obtain dynamic change process of the crack, and specifically comprises steps of:

Step Z1, adjusting, after a stable second leaking stoppage layer is formed, the pressure value of the first back pressure valve (10) to be equal to a value of the inlet pressure gauge (8), and leading the excess leaking stoppage slurry into the recycle pool (4) through the first back pressure valve (10) so that the leakage leaking stoppage slurry inside the fluid inlet channel (17) and the inverted corner (18) of the crack simulation mechanism form a dynamic flow;

Step Z2, increasing a flow rate of the hydraulic pump (5) to 3 L/min and keeping for 1 h;

Step Z3, increasing the flow rate of the hydraulic pump (5) to 4 L/min and still keeping for 1 h;

Step Z4, increasing the flow rate of the hydraulic pump (5) with an increment of 1 L/min per hour until the leakage stoppage layer (200) is damaged;

Step Z5, recoding change of the pressure value of the pressure sensor (19) as an function of time, and recording, when it is observed that the pressure value of the pressure sensor (19) changes suddenly, a position of a pressure measurement point on a seam plate (13) that corresponds to the pressure sensor (19) to determine leaking stoppage location of the leaking stoppage slurry in the crack; and Step Z6, plotting a curve regarding a relationship between the pressure value of the pressure measuring point on the seam plate (13) and the flow rate.

\* \* \* \* \*